United States Patent [19]

Calandra et al.

[11] Patent Number: 5,094,955
[45] Date of Patent: * Mar. 10, 1992

[54] DEVICE AND METHOD FOR DETECTING MICROORGANISMS

[75] Inventors: Michael J. Calandra, Somerset, N.J.; James E. Turner, Chapel Hill, N.C.; Thurman C. Thorpe; James L. DiGuiseppi, both of Durham, N.C.; Richard C. Driscoll, Raleigh, N.C.; Carmella S. Moody, Oxford, N.C.

[73] Assignee: Akzo N.V., Arnhem, Netherlands

[*] Notice: The portion of the term of this patent subsequent to Jul. 31, 2007 has been disclaimed.

[21] Appl. No.: 480,398

[22] Filed: Feb. 15, 1990

Related U.S. Application Data

[63] Continuation-in-part of Ser. No. 322,874, Apr. 13, 1989, which is a continuation-in-part of Ser. No. 168,291, Mar. 15, 1988, Pat. No. 4,945,060.

[51] Int. Cl.$^5$ .............................................. C12M 1/34
[52] U.S. Cl. ....................................... 435/291; 435/34; 435/287; 435/313; 435/807; 436/196; 422/52; 422/68.1
[58] Field of Search ............... 435/291, 289, 288, 287, 435/284, 286, 296, 34, 29, 313, 807, 808; 436/146; 422/68, 52

[56] References Cited

U.S. PATENT DOCUMENTS

| | | |
|---|---|---|
| Re. 31,879 | 5/1985 | Lubbers . |
| 2,880,070 | 3/1959 | Gilbert et al. . |
| 3,067,015 | 12/1962 | Lawdermitt . |
| 3,676,679 | 7/1972 | Waters .................. 435/291 |
| 3,853,712 | 12/1974 | House et al. ............ 435/289 |
| 3,998,591 | 12/1976 | Eckfeldt . |
| 4,004,981 | 1/1977 | Hurni et al. ............. 435/285 |
| 4,073,691 | 2/1978 | Ahnell et al. ........... 435/291 X |
| 4,101,383 | 7/1978 | Wyatt et al. . |
| 4,152,213 | 5/1979 | Ahnell .................... 435/34 |
| 4,182,656 | 1/1980 | Ahnell et al. ............ 435/34 |
| 4,289,248 | 9/1981 | Lynn ....................... 215/330 |
| 4,306,877 | 12/1981 | Lubbers . |
| 4,407,959 | 10/1983 | Tsuji et al. . |
| 4,456,380 | 6/1984 | Kondo et al. . |
| 4,568,518 | 2/1986 | Wolfbeis et al. ........ 436/163 |
| 4,672,039 | 6/1987 | Lundblom ............... 435/291 |
| 4,698,308 | 10/1987 | Ikeda ....................... 435/291 |
| 4,780,191 | 10/1988 | Romette et al. ......... 435/291 X |
| 4,784,947 | 11/1988 | Noeller . |
| 4,971,900 | 11/1990 | Ahnell ..................... 435/34 X |

FOREIGN PATENT DOCUMENTS

| | | |
|---|---|---|
| 472420 | 5/1976 | Australia . |
| 0104463 | 4/1984 | European Pat. Off. . |
| 0301699 | 2/1989 | European Pat. Off. . |
| 0333253 | 9/1989 | European Pat. Off. . |
| 2603684 | 3/1988 | France . |
| 57-207861 | 12/1982 | Japan . |
| 61-149818 | 7/1986 | Japan . |

OTHER PUBLICATIONS

"Optical Sensors for pH and Blood Gas Analysis", H. J. Marsoner et al., IFCC Workshop, Helsinki 1985.
"Simplex Optimization of a Fiber-Optic Ammonia Sensor Based on Multiple Indicators", T. D. Rhines et al., 60 Anal. Chem. 76-81 (1988).
"Fiber-Optic Fluorescing Sensor for Ammonia", O. S. Wolfbeis et al., 185 Analytica Chemica Acta 321-327 (1986).

Primary Examiner—Larry Jones
Attorney, Agent, or Firm—Donna Bobrowicz; William M. Blackstone

[57] ABSTRACT

An instrument and a sealable vessel for detecting the presence of microorganisms in a specimen, the vessel containing a liquid culture medium communicating with a sensor means containing an indicator medium therein. Changes in the indicator medium resulting from pH change or change in $CO_2$ concentration in the medium are detected from outside the vessel.

21 Claims, 7 Drawing Sheets

DEVICE AND METHOD FOR DETECTING MICROORGANISMS

This application is a continuation-in-part of application Ser. No. 07/322,874, filed Apr. 13, 1989, which is a continuation-in-part of application Ser. No. 07/168,291, filed Mar. 15, 1988 now issued as U.S. Pat. No. 4,945,060.

The present invention provides a device and apparatus for continuously monitoring changes in pH or $CO_2$ in a specimen using a growth medium and sealed container without entering into the container after the sample is prepared and the container sealed. As further advantages, the invention prevents constituents in the specimen from affecting colorimetric determinations and also provides a means for essentially continuously monitoring the pH or the $CO_2$ concentration in the specimen.

BACKGROUND OF THE INVENTION

The presence of microbial contamination in clinical specimens is conventionally determined by culturing the specimens in the presence of nutrients and detecting microbial activity through changes in the specimen or in the atmosphere over the specimen after a period of time. For example, in U.S. Pat. No. 4,182,656 to Ahnell et al the sample is placed in a container with a culture medium comprising a carbon 13 labelled fermentable substrate. After sealing the container and subjecting the specimen to conditions conducive to biological activity, the ratio of carbon 13 to carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the pressure of the gas in the container. U.S. Pat. No. 4,073,691 provides a method for determining the presence of biologically active agents, including bacteria, in a sealed container containing a culture medium by measuring changes in the character of the gaseous atmosphere over the specimen after a period of time. A method for non-invasive detection of $CO_2$ changes in the gaseous atmosphere is taught by Suppman et al, as disclosed in EPO application 83108468.6, published Apr. 4, 1984. The methods and apparatus described in these and other publications all require either a radiometric method or the invasion of the sealed container to measure changes in the gaseous atmosphere after culturing or require special materials that permit infra-red light to pass.

Other known methods for measuring microbial contamination of specimens, particularly blood cultures, include measuring minute changes in temperature, pH, turbidity, color, bioluminescence, and impedance. Generally, these methods determine microbial contamination by detecting bacterial metabolic byproducts. Microbial contamination may also be assessed by subculturing and/or staining. Of these methods, only impedance, radiometry and infra-red spectrometry provide the possibility of automated processing of clinical specimens. And except for impedance and infra-red measurements, these procedures also require entering the container in order to make a measurement on the liquid specimen or the gaseous atmosphere over the specimen. In addition to the likelihood of contamination and creating the likelihood of altering the constituency of the atmosphere over the specimen each time a determination is made, these methods do not permit taking measurements continuously or repeatedly over short time intervals for an extended period of time. This is a significant disadvantage as the rate of growth of contaminating organisms differs depending on the organism and the number of organism in the original sample, such that it cannot be predicted when detectable changes in the atmosphere or fluid sample will be presented by a contaminated specimen. In a related problem, when contamination is determined by pH changes in the liquid sample, various metabolic products will affect the pH of the sample differently. For example, the production of ammonia will raise the pH while the production of $CO_2$ will lower it. Different growth rates of different contaminating organisms could result in a pH increase at one time and a decrease at another time, which would not be detected if the pH is measured at widely spaced intervals. Another source of error when detecting changes by pH measurement in whole blood samples, particularly when an indicator dye is the means for pH determination, is the likelihood that the dye appearance can be affected or obscured by the presence of blood cells. Colorimetric indicators can only be effectively used if errors induced by the nature of the specimen can be prevented from influencing the appearance of the dye.

SUMMARY OF THE INVENTION

The present invention relates to an apparatus and a device for detecting the presence of microorganisms in clinical specimens, such as blood or other body fluids, and in non-clinical specimens, by culturing the specimens with a sterile growth medium in a transparent, sealed container. The presence and the identification of microorganisms is determined by detecting or measuring changes in the pH of the specimen or the production of $CO_2$ within the specimen using a sensor affixed to the interior surface of the container or to the sealing means used to seal the container. According to this invention, microorganisms can be detected in the presence of interfering materials, such as large concentrations of red blood cells, through non-radiometric and non-invasive means.

Figure 1:
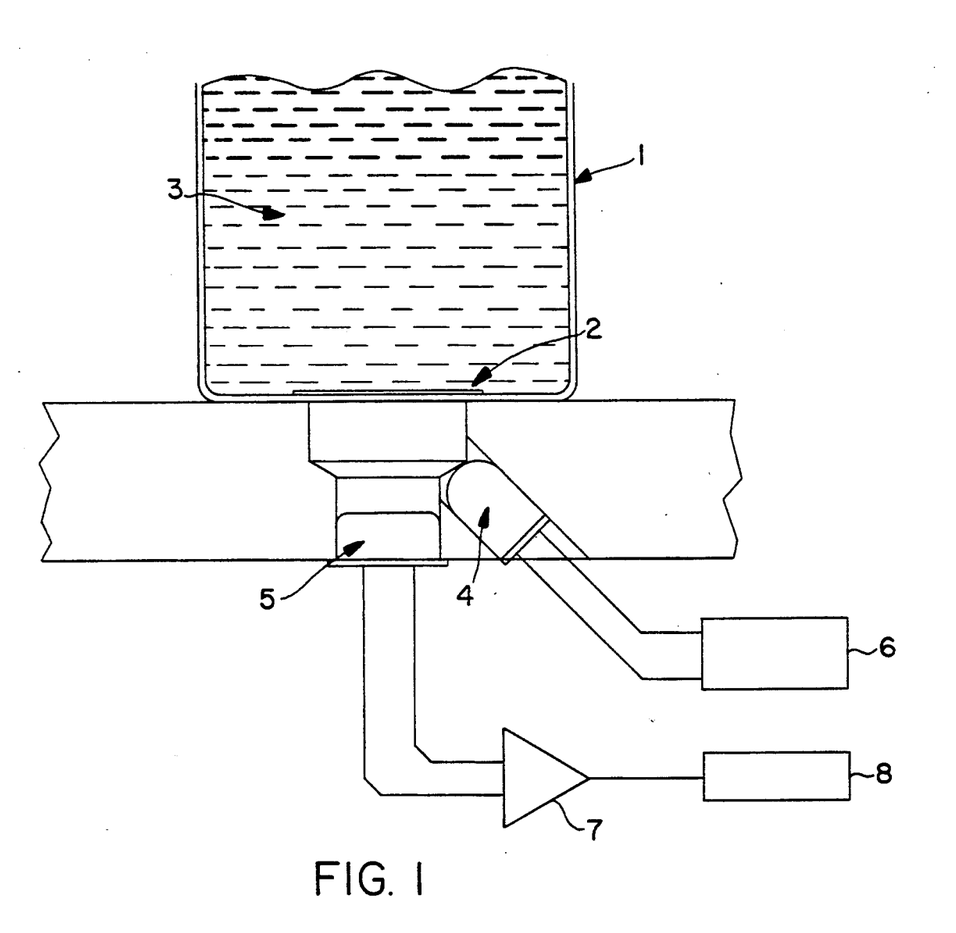
FIG. 1—Blood culture instrument

This drawing show the overall appearance of the functional part of the instrument, the detector assembly, with (1) the vessel, (2) sensor, (3) culture medium, the (4) light source, (5) photodetector, and the associated electronics including (6) current source, (7) current to voltage converter and (8) low pass filter.

Each detector assembly preferably consists of a photodiode in a countersunk hole and one or more LED's arrayed such that light falls on the surface to be viewed, but not directly onto the detector itself. The electronic circuits in this embodiment include amplifiers and filters to condition the signals from the detectors, multiplexers to select among the signals available, and constant current sources for the illuminators.

In operation, the entire device is placed on an agitator inside a 37° C. incubator, which provides a suitable environment for microbial growth and excludes room light from the photodetectors.

Figure 2:
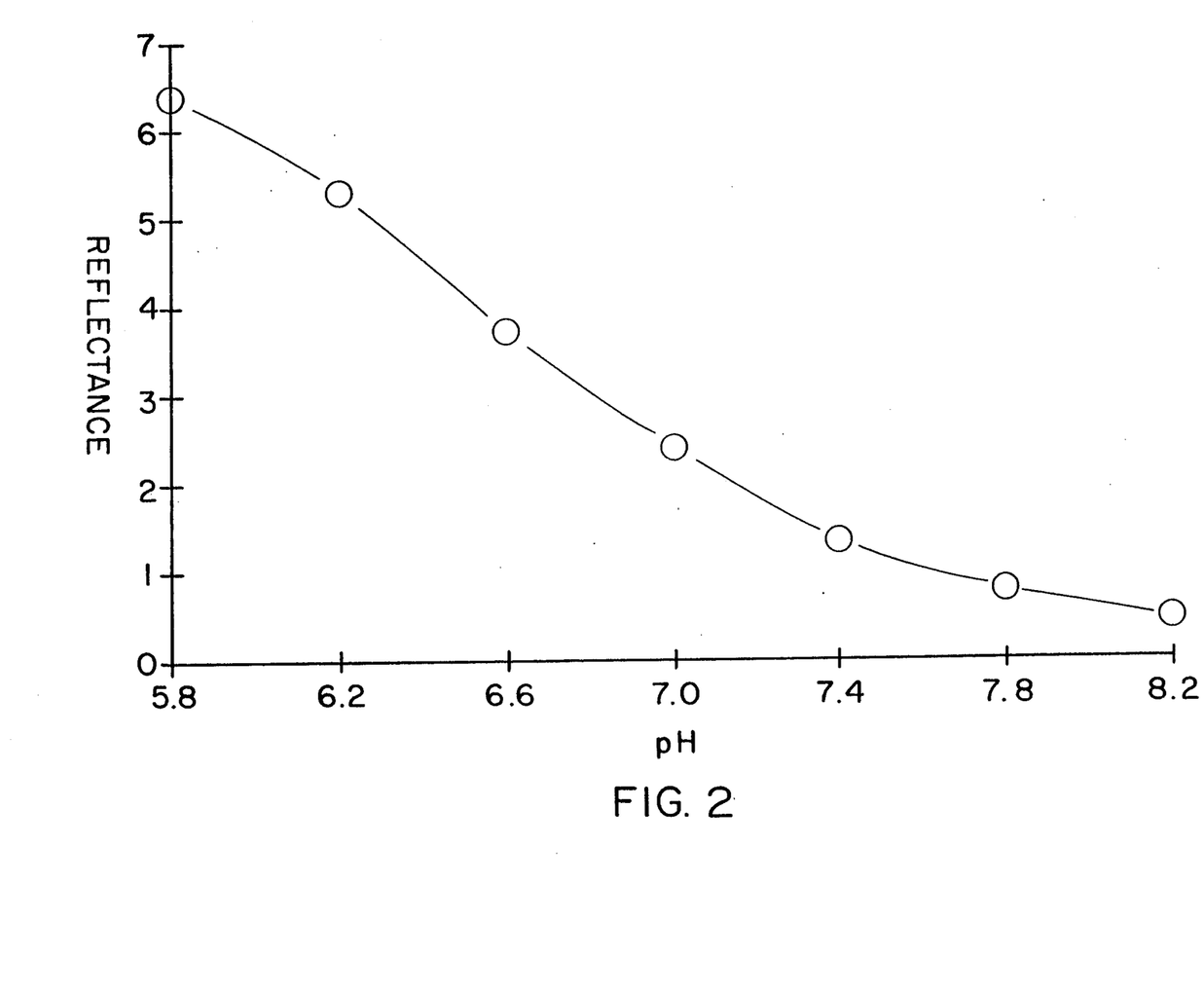
FIG. 2—pH Sensitivity

Besides testing the instrument subjectively with various colored bottles, it was tested with the pH sensitive membrane bottles. This figure shows the average voltage output of seven different detectors after equilibration of the sensor with various buffers over a pH range of 5.8 to 8.2. Detailed studies showed that the system could reliably distinguish changes of 0.1 pH unit over a range of pH 6.0 to 7.5.

Figure 3:
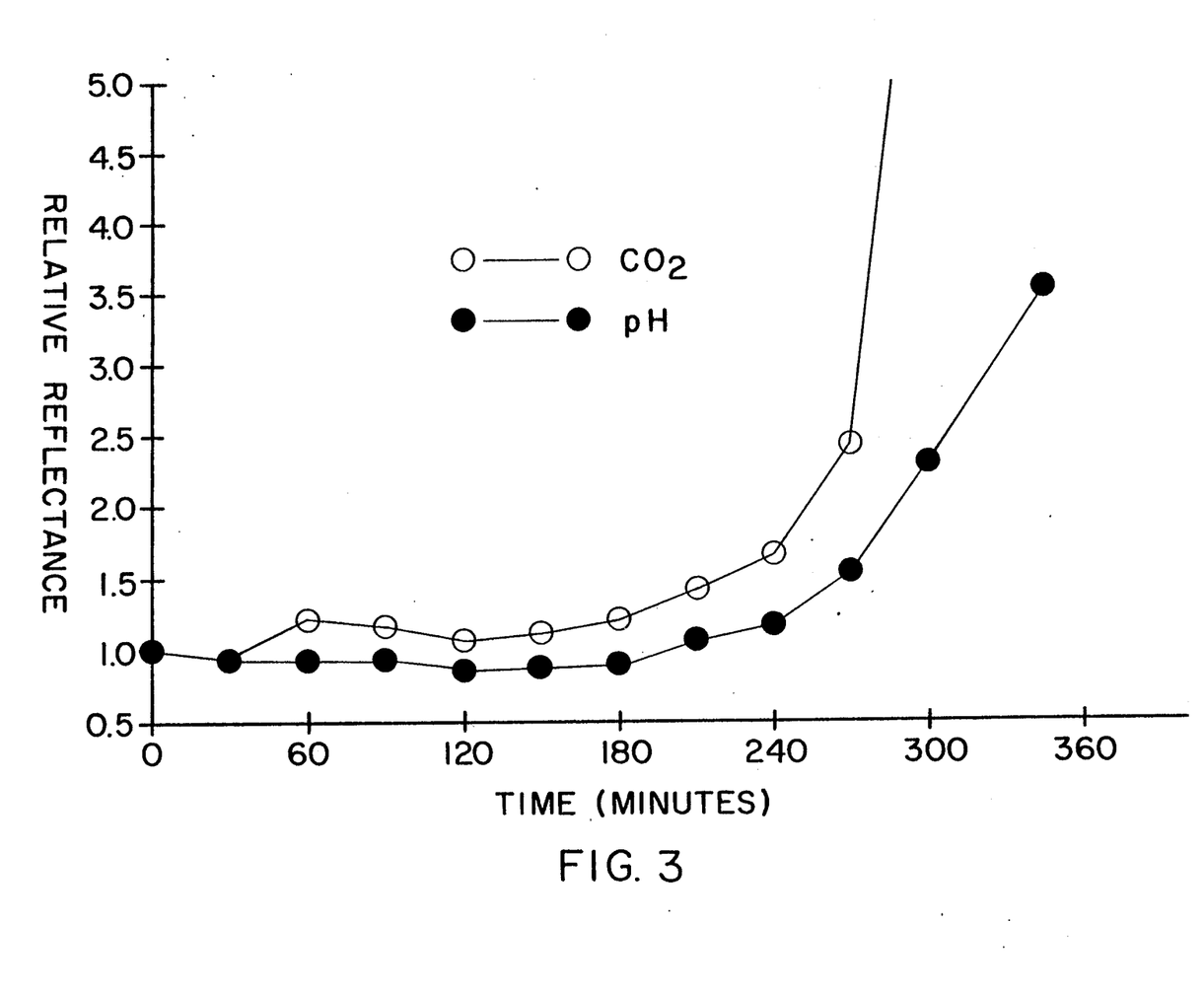
FIG. 3—pH and $CO_2$ change with microbial growth

The instrument was used to detect microbial growth by both pH change and by $CO_2$ production. This figure shows the change in pH and in $CO_2$ resulting from growth of the bacterium, *E. coli*.

Figure 4:
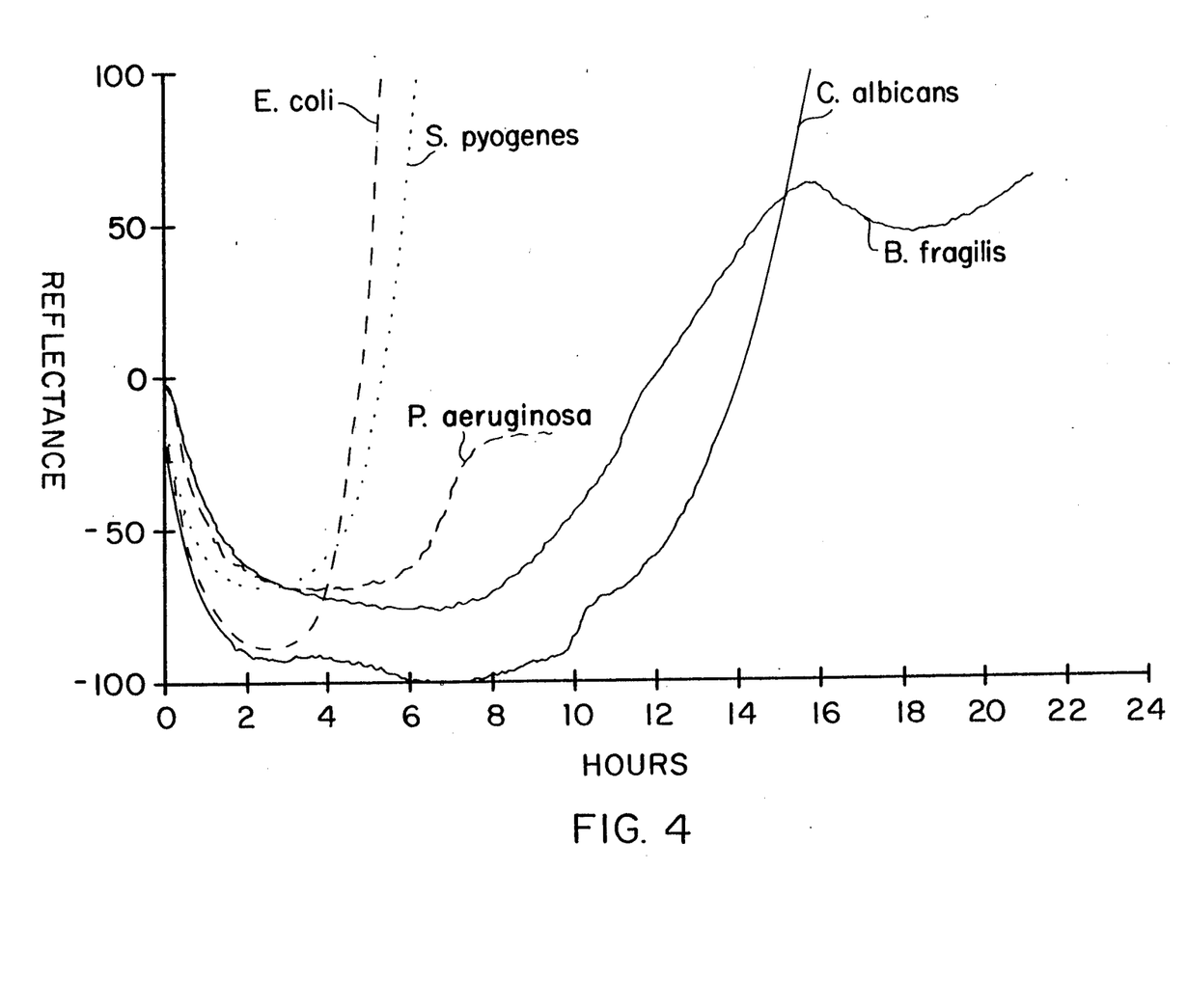
FIG. 4—Detection of a variety of microorganisms

Essentially all organisms will release $CO_2$ in the course of their metabolism. Thus, this system can be used to detect the growth of a very wide range of microorganisms. This figure shows the detection of $CO_2$ produced during the growth of *E. coli*, a Gram negative bacterium; *S. pyogenes*, a Gram positive bacterium; *P. aeruginosa*, a Gram negative non-fermenting bacterium; *B. fragilis*, an anaerobic bacterium; and *C. albicans*, a yeast. The units indicate relative $CO_2$ concentration in the medium based on $CO_2$ concentration at the beginning of the assay. Because the sample containers and media are at room temperature (approximately 20° C.), and the container and sample are incubated at 37° C. during the assay, $CO_2$ is released into the space above the liquid sample and medium during the first 2 to 4 hours because of the reduced solubility of $CO_2$ in the liquid as temperature increases. Unless the containers and media are maintained at the higher temperature before introduction of the sample and placement into the instrument, reliable indication of the presence of microorganisms cannot be measured until after the minimum $CO_2$ concentration is passed, typically within the first 2 to 4 hours.

Figure 5:
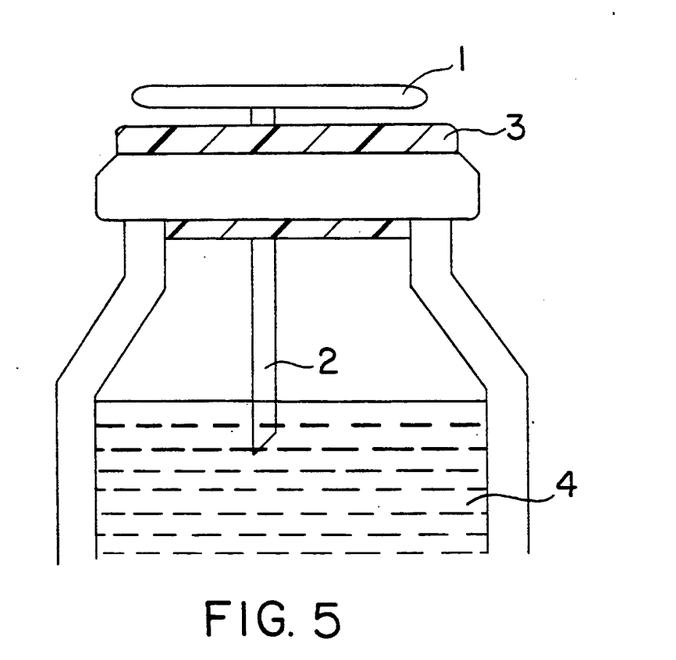
FIG. 5—Sensor device

This figure shows (1) a sensor with (2) a cannula piercing means inserted through (3) a stopper into a (4) culture container.

Figure 6:
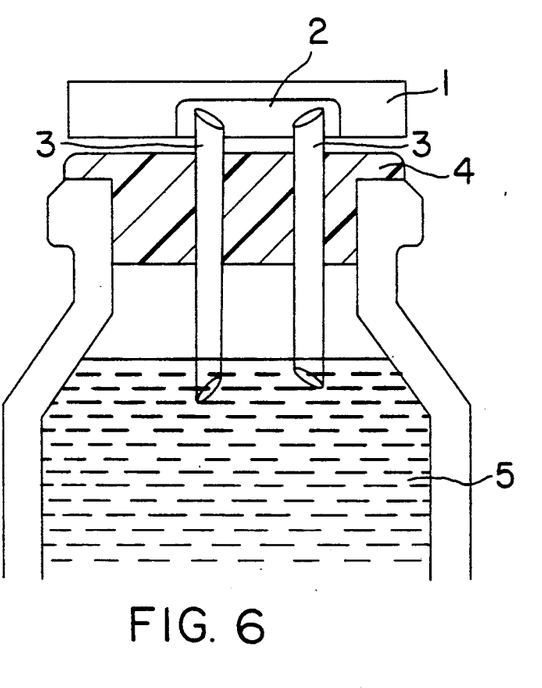
FIG. 6—Sensor device

This figure is a cross-sectional view of (1) a sensor with (2) a passage connecting two (3) cannula piercing means, to provide greater contact of gases and sample with the indicator, which is inserted through (4) a stopper into (5) a culture container.

Figure 7:
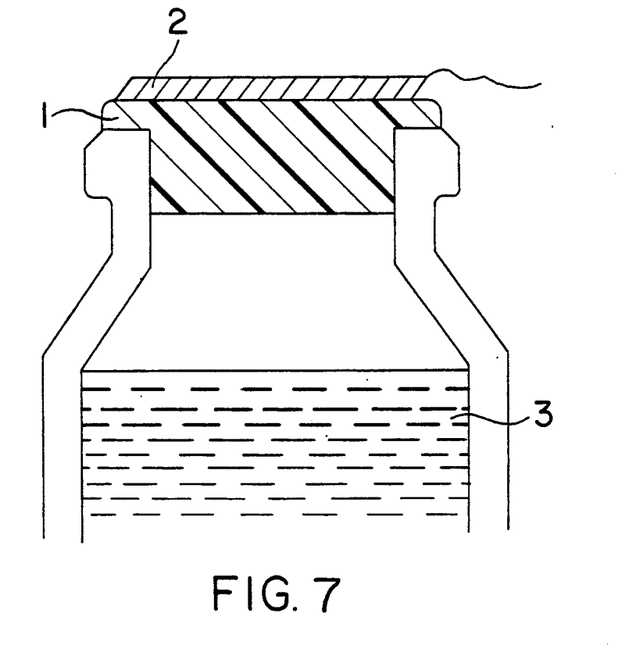
FIG. 7—Piezoelectric sensor device

This figure is a cross-sectional view of (1) a sensor device that incorporates (2) a piezoelectric strip as part of the sealing means, which emits a signal when a change of pressure occurs inside (3) the container.

DESCRIPTION OF PREFERRED EMBODIMENTS

The apparatus and device of the invention provide a non-invasive means for detecting the presence of microorganisms in clinical specimens, such as blood samples or other body fluids, and in non-clinical specimens by measuring an increase in metabolic products produced by microorganisms. The specimen is added to a specially formulated medium that enhances the production of certain microbial metabolic products, which are detected by a unique disposable sensor located at the bottom of a culture container or in the sealing means of the container. The sensor comprises a solid composition or membrane, which we refer to as an attachment or support medium, with an indicator medium immobilized on or within it. The sensor is located flush against the inside surface of a container, in the sealing means used to seal the container or attached to the sealing means, such that the indicator medium is visible from outside. It may be affixed to the container to prevent cells, proteins, other solids or other opaque or colored components from getting between it and the container surface. In certain embodiments the sensor is separated from the specimen and its growth medium by a membrane or solid layer that permits the passage of gas molecules but prevents passage of ions.

A preferred embodiment of this invention comprises a sealing means, such as a cap or lid, which may be transparent or which may have a transparent section. The sensor is placed in proximity to the transparent cap or section of cap or is made part of the cap. When the cap is used to seal the container, the changes in indicator are read through the transparent sealing means. An advantage seen to this embodiment is that this may be the most economical way to produce the containers on a large scale.

More preferably, the sealing means may be made of a material, such as a polymer, which contains encapsulated indicator micelles. A transparent section in either the container or the sealing means is not needed, as long as the material is permeable to the metabolic products of the microorganisms and the changes in the indicator are visible on the surface of the sealing means.

Another embodiment of this invention is a sensor that is attached to at least one hollow piercing means, such as a cannula, as seen in FIG. 5. The indicator medium in the sensor is in communication with the hollow center of the cannula. The container is sealed with a conventional stopper, such as a rubber stopper. The sensor device is placed on the stopper and the cannula pierces through the septum of the rubber stopper into the container. The inoculated medium, gaseous metabolic products from the microorganisms, or gases from the medium itself, travel up the cannula and change the color of the indicator in the sensor, which is then read. An improvement on this embodiment is the use of one, but preferably at least two cannulas that each have one end in the sensor in communication with the indicator, preferably an open passage connecting the one end of each cannula, as seen in FIG. 6. The sensor may be a solid polymer emulsion, or a cast plastic piece that contains the sensor, or any other type of device that incorporates these elements. In each case, the sensor is contiguous to the connecting passage. As above, both cannulas pierce through the septum of the stopper on the container and enter into the container. When the container is agitated, the liquid and/or the gases inside the container will flow into one cannula and out the other, providing a direct contact of the specimen with the sensor.

Microorganisms in specimens of body fluids, such as blood, containing as few as 1 organism per milliliter, can be detected using this invention. Such specimens may require up to 7 days incubation before the population of organisms reaches a critical level and where an increase in metabolic products can be measured. We found a concentration of $10^6$ CFU/ml for certain types of organisms provided measurable changes in pH or $CO_2$. All organisms showed measurable results at concentrations of $10^7$ to $10^8$ CFU/ml.

The invention is unique and advantageous in several respects; (1) the microbial metabolic products are measured in the liquid phase of the culture bottle rather than in the atmosphere over the specimen, (2) because the unique disposable sensor is affixed to the interior surface of the bottle or the closure or sealing means or attached through the outside of the closure or sealing means, measurements can be made from outside the transparent wall of the bottle or the sealing means without having to violate the integrity of the bottle, (3) the external measurements can be made by visual inspection or with an instrument that measures by reflectance, (4) opaque or colored components in the specimen do not interfere with the ability of the sensor to detect changes or the measurement of those changes, and (5) a high concentration of indicator molecules is maintained within a small volume in the sensor, i.e., within the polymer emulsion or on the membrane, such that color change can be easily observed.

Another type of sensor that allows measurement of changes occurring inside the culture bottle without entering into the container is the embodiment comprising a piezoelectric apparatus, such as a piezoelectric strip, that is attached to the cap, i.e., the closure or sealing means as seen in FIG. 7. The signal from the apparatus is automatically zeroed when the container and its contents reach incubation temperature. The apparatus is distorted as the closure expands from the pressure of the metabolic products produced by microorganisms. The electrical signals generated from this distortion are measured to monitor the biological activity inside the container. Another embodiment is a device, separate from the container, which is attached through the sealing means of the container. For example, this embodiment can be a solid rubber rectangle which contains a hollow section, at the base of which is a piezoelectric strip. Beneath the strip, a cannula is inserted through the rubber rectangle. The exposed end of the cannula pierces through the sealing means of the container, entering the container. As gaseous respiration products of the microorganisms accumulate in the cannula, the pressure they exert force the rubber between the end of the cannula and the piezoelectric strip to distort and push the strip into the hollow section. The electrical signal produced by the distortion of the piezoelectric strip is then measured.

Another embodiment of the above device is the use of more than one cannula, thereby increasing the amount of gas that enters the rubber device. The use of two cannulas permits easier flow into and out of the sensor, such as a tide-like flow when the bottle, laying on its side, is tilted.

The nutritional components that make up a complex microbial medium influence the metabolic pathways used by microorganism. Organic acids, bases and various gases are produced in proportions dependent on the nutrients available. These products also vary from species to species of microorganism. The presence of these products in the liquid medium can change its pH. The sensors used in the invention contain pH sensitive indicators that give a measurable change in response to a pH change in the environment. In the embodiment in which the pH sensor is covered by a gas-permeable, ion-permeable membrane, the presence of gases that affect the pH of the indicator, such as $CO_2$ or ammonia, is measured. Thus, microbial growth can be detected either by changes in pH of the liquid culture medium or by measurement of gases dissolved in the medium, both indications are caused by metabolic gaseous products produced by microorganisms. Carbon dioxide is a universal metabolite produced by all organisms and, therefore, is the preferred metabolite for detection of microbial growth.

$CO_2$ and pH sensors share two common components, a molecular species useful as a pH indicator and an attachment/support medium. The pH indicator can be attached either covalently or non-covalently to the support medium. Alternately, the indicator can be encapsulated within a polymer matrix such as being emulsified within a polymer matrix prior to curing. To perform as a pH sensor, indicator must be in contact with the liquid medium. The $CO_2$ sensor has a third component, a semi-permeable substance that completely separates the indicator membrane from the specimen and growth medium. The semi-permeable layer may be a separate membrane, alternatively, the cured polymer adjacent to the specimen and growth medium may form an integral semi-permeable membrane. These sensors are affixed inside a suitable transparent vessel or a transparent sealing means with an appropriate adhesive. They may also comprise an integral part of the sealing means or be affixed to the sealing means or within the vessel as an indicator emulsified within a polymer matrix cured in situ. They can also be placed outside the container, as long as a method is provided that allows the metabolic products of the microorganisms or the growth medium containing the specimen to contact the sensor.

A variety of different fluorescent and visible pH indicators can be used as the active molecular species in pH or $CO_2$ sensors. Generally, the only limitations on the selection of indicators are the requirements that they have acceptable dynamic pH ranges and wavelength changes that are readily detectable by existing front surface fluorescence or reflectance technologies.

Sensors for detecting pH changes in the culture medium according to the invention preferably exhibit a change in fluorescence intensity or visible color over a pH range of about 5.0 to bout 8.0.

Indicators for the $CO_2$ sensor should exhibit a change in fluorescence intensity or visible color preferably between about pH 13 and about 5, and most preferably between about pH 13 to about 9, in order to detect changes in $CO_2$ concentration.

Only certain pH indicator molecules can be bound covalently or non-covalently to a support medium and retain their pH indicating properties. We found indicators belonging to the xanthene, phenolphthalein and phenolsulfonphthalein groups to be useful. Examples of these include fluorescein, coumarin, phenolphthalein, thymolphthalein, byomothymol blue, thymol blue, xylenol blue and a-naphthol benzein.

The attachment/support medium can be a substance such as cellulose, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with the microbial growth medium.

The pH indicator sensors directly detect pH changes due to the pH environment of the microbial growth medium. However, these sensors can be made to selectively react to gases (e.g., carbon dioxide, ammonia) in the liquid growth medium by covering them with a selectively semi-permeable composition or membrane, such as silicone, latex, teflon, or various plastics characterized by the capacity to selectively permit the diffusion of a gas while preventing the passage of ions. For sensors comprising indicator encapsulated within a polymer matrix, the polymer forming the matrix can act as the semi-permeable barrier that permits the passage of gases but not ions.

In the encapsulated indicator embodiment, the $CO_2$ sensor is comprised of four components. The first component is a visual or fluorescent pH indicator, which is reactive at the pH range between 6 and 10. Examples of indicators meeting these criteria are bromothymol blue, thymol blue, xylenol blue, phenolphthalein, coumarin, and fluorescein. The second component is sodium hydroxide or an equivalent base, which maintains an optimal pH environment for detection of $CO_2$ by the selected pH indicator. The third component is glycerol or an equivalent emulsifier, which can produce droplets of indicator solution emulsified within the uncured polymer. The fourth component is the uncured polymer such as silicone, which maintains a proper environment for the indicator. Any polymer can be used that does not affect the chemical activity of the indicator, either from its own chemical or physical properties or its requirements for curing, as long as it is permeable to gases but not ions, and does not have these properties altered when subjected to sterilization. Other silicone polymers that are also satisfactory are those that are curved by high temperature, by catalytic activity, or by ultraviolet vulcanization. An emulsion is prepared from the four components and the polymer is cured to form a semipermeable matrix around the droplets of pH indicator, which permits selective diffusion of $CO_2$ and other gases from the liquid microbial growth medium, resulting in a measurable change in the indicator. The sensor can be prepared separately, such as in a mold, cured, and then attached to the culture bottle with an appropriate adhesive, such as a silicone adhesive. Alternatively, and preferably, the sensor is formed on the bottom of the bottle and cured in situ. After curing the bottle with the sensor is sterilized, such as by autoclaving. Conveniently, the growth medium can be introduced into the bottle before autoclaving and also sterilized by that process.

Another alternative is to spray the sensor onto the inside surface of the container, such as the bottom of a microtiter plate, to form a thin layer. Suitable media, which may be non-sterile, is added to each well, and inoculated with the specimen. It has been found that these plates generally need only a 4-6 hour incubation period to record a color change in the sensor.

The specific examples of sensors that follow are provided to illustrative various uses of the invention, but not limit its scope as claimed.

EXAMPLE 1

Preparation of Non-fluorescent Indicator pH Sensors

Nylon membranes modified to have positive zeta potentials (Zeta Probe, BioRad) were placed in a 3% solution of Tryptic Soy Broth and soaked for one hour at room temperature with gently shaking on a rotating shaker. Excess Tryptic Soy Broth was exhaustively washed from the nylon membranes with deionized water. The washed membranes were placed in a 0.0001 to 0.1% solution of pH indicator (bromothymol blue) dissolved in 0.1 N NaOH. The membranes were allowed to react for one hour at room temperature with gentle shaking. Excess indicator solution was removed from the membranes by exhaustively washing with deionized water until no indicator appeared to be washed from the membranes. The pH indicator membranes were allowed to air dry for 24 hours and 11/16 inch circles were punched from the membranes.

The pH indicator membranes were attached to the bottom of glass vessels with a silicone adhesive (GE 2501 Silicone Sealant, clear. These bottles were filled with microbial growth medium and sterilized by autoclaving.

EXAMPLE 2

Preparation of Non-Fluorescent Indicator $CO_2$ Sensors

Nylon membranes modified to have positive zeta potentials (Zeta Probe, BioRad) were placed in an indicator solution comprised of 0.001 to 0.1% xylenol blue and 0.0001 to 0.1% bromothymol blue dissolved in 0.1 N NaOH. The membranes were allowed to react for one hour at room temperature with gentle shaking. After reacting with the indicator solution, the membranes were exhaustively washed with deionized water to remove excess indicator. The indicator membranes were air dried for 24 hours and 11/16 inch circles were punched from the membranes. The indicator membranes were then attached to the bottom inside surface of clear glass bottles with silicone adhesive (GE 2501 Silicone Sealant II, clear) and a second layer of the silicone adhesive was placed on top of the indicator membrane to completely seal the nylon indicator membrane.

These bottles were filled with microbial growth medium and sterilized by autoclaving.

EXAMPLE 3

A. Preparation of Encapsulated Indicator Sensors

Stock solutions were prepared of 0.1–1.0% phenolphthalein, xylenol blue, or bromothymol blue in 0.0005–0.5 N NaOH containing 25–75% glycerol. 0.1–0.5 ml of the stock indicator-NaOH-glycerol were added to 1.0 gram of uncured RTV white silicone (GE Silicone II, white) and mixed until a fine emulsion was made. The silicone-indicator emulsion was placed into a syringe dispenser and dispensed 0.1–0.2 ml into the bottom of a glass bottle and the emulsion distributed evenly on the bottom of the glass bottle. The indicator-silicone emulsion sensor was allowed to cure for a minimum of 24 hours at ambient temperature in at atmosphere of less than 50% relative humidity. After curing, the bottles with $CO_2$ sensors were filled with microbial growth medium and sterilized by autoclaving.

B. Apparatus for Automatic Detection of Microbial Contamination

Both pH change and $CO_2$ production due to microbial growth may be detected and measured using the instrument described in copending U.S. patent application Ser. Nos. 07/322,874, 07/168,291, and 07/351,476, filed on May 15, 1989, which are incorporated herein by reference.

The sensors monitored by this instrument contain indicators that change color when growing or metabolizing microbes are present. Although the color changes may be apparent to the naked eye, use of the instrument provides the advantages of objectivity, sensitivity, and continuity of measurement. In the preferred embodiment the instrument is essentially a visible light reflectometer that monitors the color change of the sensor. In order to allow continuous monitoring of all samples, it is preferred to have a detector for each sample. Other alternatives will be obvious to those skilled in the art, such as using conventional means to move specimen containers past one or more stationary detectors or moving one or more detectors past stationary specimens.

In the preferred embodiment solid state illuminators and detectors are used. Incandescent and arc lamp sources of illumination may also be used in conjunction with mirrors, lenses, optical fibers, and other means of directing the light to the sensor.

C. Culture Medium Formulations

The medium used for microbial detection by a change in pH in the instrument described in Example 3 B above comprised 3% Tryptic Soy Broth (DIFCO), 0.5% Proteose Peptone (DIFCO) #3, 1.25% D-glucose, 1% L-arginine, 0.01% L-cysteine, and an anticoagulant, 0.05% SPS sodium polysulphonate. This medium has a low buffering capacity so that any metabolic products that affect pH will easily change the pH of the medium. Glucose is a fermentable carbohydrate that when metabolized by microorganisms results in the production or organic acids that cause a decrease in pH. Arginine is added as a substrate for those non-fermenting microorganisms (i.e. *Pseudomonas aeruginosa*) that do not normally metabolize glucose. The addition of arginine results in release of basic metabolites that cause an increase in pH of the medium. If $CO_2$ production by *Pseudomonas aeruginosa* is to be measured, argninine is not included. Other carbohydrates or amino acids can be incorporated into the medium to induce pH change when metabolized by other species of microorganisms.

D. Tests Using Seeded Cultures

Bottles as described above in 3 A were filled with 30 ml of the medium of 3 B above and sterilized by autoclaving. Each bottle was inoculated with one of the organisms listed on Table 1. The bottles were placed in the instrument as described above, and inoculated at 35° C. for 24 to 48 hours. When a change was noted in the sensor, the bottle was recorded as containing a microorganism.

The microorganism listed in Table 1 have been detected using the invention as described above.

TABLE 1

| Organisms Detected in Seeded Cultures | |
|---|---|
| Enterobacteriaceae | Nonfermentors |
| Escherichia coli | Pseudomonas aeruginosa |
| Enterobacter cloacae | Pseudomonas putrifaciens |
| Citrobacter freundi | Xanthomonas maitophilia |
| Klebsiella pneumoniae | Acinerobacter sp. |
| Providencia rettgeri | Eikenella corrodens |
| Proteus mirabilis | Moraxella sp. |
| Salmonella Group B | Achromobacter Group VD |
| Serratia marcesans | Anaerobes |
| Yersinia enterocolitica | Bacteroides fragilis |
| Staphylococcus spp. | Bacteroides melaninogenicus |
| Coagulase - negative staphylococcus | Bacteroides asaccharolyticus |
| | Clostridium perfringens |
| S. aureus | Fusobacterium necrophorum |
| Streptococcus spp. | Veillonella parvula |
| S. pneumoniae | Peptostreptococcus anaerobius |
| Group A | Peptococcus magnus |
| Group B | Peptococcus asaccharolyticus |
| Group C | Bacteroides ovatus |
| Group D - non enterococci | Eubacterium limosum |

TABLE 1-continued

| Organisms Detected in Seeded Cultures | |
|---|---|
| Enterococci | Eubacterium alactolyticum |
| Viridans group streptococci | Other Microorganisms |
| Nutritionally variant streptococcus | Haemophilus influenzae |
| | Haemophilus parainfluenzae |
| Yeast | Neisseria meningitidis |
| Candida albicans | Vibrio parahemoliticus |
| Cryptococcus neoformans | Neisseria gonorrhoeae |
| Rhodotorula rubra | Branhamella catarrhalis |
| Torulopsis glabrata | Aeromonas hydrophilia |
| | Listeria monocytogenes |
| | Gardnerella vaginalis |
| | Campylobacter jejuni |

These results indicate that these, any other organisms of the same type, and any organisms that produce detectable gases or that affect the pH of the liquid medium can be detected using the invention.

Although a specimen containing a pure culture is the most preferable sample to test, other specimens containing a single predominating organism, such as an infected body fluid, a solid that is fluidized, a rinsate from a solid, or other turbid fluids, such as those found in food processing plants, manufacturing sites, meat packing plants or lakes and streams, may be used as the inoculum. In particular, blood drawn from a blood culture bottle may be directly inoculated into prepared microtiter wells and the results usually read within four to six hours, although some microorganisms may take up to 24 hours to produce a color change in the sensor. Thus, organisms in positive specimens can be identified by directly inoculating appropriately prepared microtiter wells with the positive culture, such as from a blood culture bottle, and incubating until characteristic growth patterns emerge.

EXAMPLE 4

Preparation of Non-fluorescent Emulsion Indicator Sensors

This sensor incorporates Eastman Kodak's Universal Indicator solution, which changes colors from pH 4 to 10.

A. Preparation of Universal Indicator 50 ml volume of a Universal Indicator solution in isopropanol obtained from Eastman Kodak Company, Rochester, N.Y., was evaporated to dryness by heating at 40° C. under reduced pressure in a rotary evaporator. The solution was re-dissolved in 4 ml of HPLC grade isopropanol. 10 microliters of 10 N NaOH was added to 2 ml of the concentrated Universal Indicator.

B. Preparation of Silicone Emulsion 10 grams of GE Silicone RTV 615 component A (General Electric Company, Waterford, N.Y.) was dispensed into a glass vial. Two milliliters of the Universal Indicator/NaOH solution, 1 gram of glycerol and 0.3 grams of a white silicone pigment were added to the silicone A component. The four components were hand mixed by gently stirring with a teflon rod. After the material was thoroughly mixed, 1 gram of GE silicone RTV 615 component B was added to the emulsion. The emulsion was gently mixed as before, by hand stirring. The emulsion was degassed in a vacuum dessicator for approximately 5 minutes. The emulsion was then transferred into a pressurized syringe dispenser fitter to an "air brush" sprayer. The silicone emulsion sensor was sprayed into 96 well polystyrene microtiter plates that had been previously coated with GE silicon primer SS 4120.

Although Example 4 used the universal indicator as the pH indicator, other indicators such as those listed in Table 2 and taken from Dawson et al, Data for Biochemical Research, 2nd edition, p. 623, Claredon Press, Oxford, 1969, are acceptable.

The negative control well contains no carbon source. The positive control well contains an undefined, rich medium. Each well is then inoculated with approximately $10^6$ organisms/well of specimen. The microtiter plate is sealed such that each individual well is sealed off from the others, and incubated at 35° C. for up to six hours. The microtiter plate is checked for color changes at hourly intervals, beginning at one hour after incuba-

TABLE 2

ACID-BASE INDICATORS

| Indicator (common name) | Preparation 0.1 g in 250 ml | Acid colour | Basic colour | pH range |
|---|---|---|---|---|
| Cresol red (acid range) | water containing 2.62 ml 0.1N—NaOH | red | yellow | 0.2–1.8 |
| m-Cresol purple (acid range) | water containing 2.72 ml 0.1N—NaOH | red | yellow | 1.0–2.6 |
| Thymol blue (acid range) | water containing 2.15 ml 0.1N—NaOH | red | yellow | 1.2–2.8 |
| Tropaeolin OO | water | red | yellow | 1.3–3.0 |
| Methyl yellow | 90% EtOH | red | yellow | 2.9–4.0 |
| Bromophenol blue | water containing 1.49 ml 0.1N—NaOH | yellow | purple | 3.0–4.6 |
| Tetrabromophenol blue | water containg 1.0 ml 0.1N—NaOH | yellow | blue | 3.0–4.6 |
| Congo red | water or 80% EtOH | violet | reddish-orange | 3.0–5.0 |
| Methyl orange | free acid: water Na salt: water containing 3 ml 0.1N—HCl | red | orange-yellow | 3.1–4.4 |
| Bromocresol green (blue) | water containing 1.43 ml 0.1N—NaOH | yellow | blue | 3.6–5.2 |
| Methyl red | Na salt: water free acid: 60% EtOH | red | yellow | 4.2–6.3 |
| Chlorophenol red | water containing 2.36 ml 0.1N—NaOH | yellow | violet-red | 4.8–6.4 |
| Bromocresol purple | water containing 1.85 ml 0.1N—NaOH | yellow | violet | 5.2–6.8 |
| Azolitmin (litmus) | water | red | blue | 5.0–8.0 |
| Bromothymol blue | water containg 1.6 ml 0.1N—NaOH | yellow | blue | 6.0–7.6 |
| Phenol red | water containing 2.82 ml 0.1N—NaOH | yellow | red | 6.8–8.4 |
| Neutral red | 70% EtOH | red | orange-brown | 6.8–8.0 |
| Cresol red (basic range) | water containing 2.62 ml 0.1N—NaOH | yellow | red | 7.2–8.8 |
| m-Cresol purple (basic range) | water containing 2.62 ml 0.1N—NaOH | yellow | purple | 7.6–9.2 |
| Thymol blue (basic range) | water containing 2.15 ml 0.1N—NaOH | yellow | blue | 8.0–9.6 |
| Phenolphthalein | 70% EtOH (60% cellosolve) | colourless | pink | 8.3–10.0 |
| Thymolphthalein | 90% EtOH | colourless | blue | 9.3–10.5 |
| Alizarin yellow | EtOH | yellow | red | 10.1–12.0 |
| Tropaeolin O | water | yellow | orange | 11.1–12.7 |

Apart from $CO_2$ and $NH_3$, which are detected using sensors containing pH indicators, other metabolic gaseous products can be monitored using indicators specific for those products. For example, a sensor according to the invention containing sodium nitroprusside as the indicator can be used to detect hydrogen sulfide.

EXAMPLE 5

Identification of Microorganisms Through Detection of $CO_2$ Production

Three thin layers of the emulsion sensor prepared in Example 4 are sprayed onto a prepared non-sterile microtiter plate. Each layer is allowed to dry prior to the application of the next layer. After the last layer of the sensor is allowed to dry, 200 microliters of media is placed into each well of the microtiter plate. The media used for the samples and the negative control is a defined, nutrient limited media, containing a different carbon source for each of twenty-three microtiter wells.

tion. When an approximately 40% difference between the negative and positive controls is seen, the plate is ready to be read. The color changes seen in each well form a total pattern of specific carbon source usage, which is used to identify the microorganism.

EXAMPLE 6

Differentiation of Microorganisms with Carbon Sources in a Microtiter Plate

A. Preparation of Carbon Dioxide Sensor Plates 50 ml Kodak Universal Indicator was evaporated to dryness and resuspended in 2 ml HPCL grade isopropanol. 240 mg of phenolphthalein, sodium salt, dissolved in 2 ml of water was added to 1 ml of the concentrated Universal Indicator solution. 150 microliters of CAPS buffer (3-{cyclohexlamino}-1-propanesulfonic acid), pH 10.4, 500 mM was mixed with the phenolphthalein-/Universal Indicator solution. This solution was added to 10 grams of GE RTV 615 A silicone that had been degassed for approximately 15 minutes. The silicone and indicator emulsion was mixed by hand stirring. 0.1 grams of white silicone pigment and 2 grams of GE RTV 615 B was added to the mixture. The mixture was hand mixed and degassed for approximately 5 minutes. The emulsion was transferred into a pressurized syringe dispenser fitted to an "air brush" sprayer and sprayed into a polystyrene 24 well plate that had previously been sprayed with 2 coats of GE silicone primer SS 4120. Enough of the indicator/silicone emulsion was sprayed into the wells to coat the bottom surface. The plate was then placed in a humidified oven and cured at 50° C. overnight. This spraying process was repeated on 3 consecutive days for a total of 3 coatings to the wells.

B. Testing Method

Two organisms, *Excherichia coli* (ATCC number 11775) and *Pseudomonas aeruginosa* (ATCC number 1014), both type strains, were grown overnight (17 hours) in a complex medium as described in Example 3 C, at 37° C., with shaking. The organisms were harvested, spun down at 11950-X-g, at 4° C. for 20 minutes. The supernatant was poured off and the organisms were resuspended in 0.9% sterile saline to an $OD_{660}=5.0$.

Each well of the prepared microtiter plate contained 1 ml of one of the following three media:

(a) a minimal medium buffered with 50 mM Hepes buffer, pH 7.2, containing no carbon source (the negative control);

(b) the same medium as the negative control except that it contained 0.5% bromosuccinic acid; and (c) an undefined medium Trypticase soy yeast extract medium, buffered with 50 mM Hepes, pH 7.2 (the positive control).

Twenty microliters of each prepared organism was added to duplicate wells of each type of media.

The wells were sealed with cork stoppers and the plate was incubated at 37° C. Color changes of the sensor on the bottom of the plate were monitored by eye over a 6 hour period. After approximately 4 hours, two distinct patterns could be seen. The negative controls for each organism did not change in color (the wells stayed purple). The positive control wells for *E. coli* changed from purple to green to yellow to orange, indicating a pH change of the sensor from 10 to approximately 6. The positive control well for *P. aeruginosa* changed from purple to green to yellow (a pH change of the sensor from 10 to approximately 7). The wells with the bromosuccinic acid medium gave the most distinction between the two organisms. This correlated with the differing ability of the two organisms to grow and produce $CO_2$ when using this carbon source. Bromosuccinic acid is a preferred carbon source of *P. aeruginosa*, whereas *E. coli* is able to utilize this carbon source only slightly to produce $CO_2$. Over a four hour period of incubation, the color change in the wells containing bromosuccinic acid and *E. coli* changed from purple to green, indicating a pH change of the sensor from 10 to 8.5. The wells containing bromosuccinic acid and *P. aeruginosa* changed in color from purple to green to yellow to orange in the four hour period. This color change indicated a pH change from 10 to approximately 6.

The sensors therefore allowed a distinction between the type strains of *E. coli* and *P. aeruginosa* with respect to their ability to utilize bromosuccinic acid as a carbon source.

Microbial Identification Based on Growth Inhibition

Microbial identification using the described $CO_2$ sensors can also be based on the principle of growth inhibition. This system differs from the classical biochemical identification systems, as identification is based on selective growth inhibition by inhibitory agents, such as dyes, antibiotics, and other substances. Once again, the production of $CO_2$ is the measure of growth. The growth pattern produced in the presence of these inhibitory agents identifies the species of the test microorganism. The amount of growth is compared with a growth control well that contains no inhibitor. A profile is derived using a two-stage quadratic discriminate analysis based on the results derived from the battery of inhibitory agents.

This identification system is a rapid method with results obtained in 3-6 hours. Once again, this system can test purified strains of microorganisms grown on agar plates as in conventional methods, but it also permits direct inoculation with body fluids such as blood, or body fluids that have been cultured to expand the microorganism population, since it is not affected by interfering substances.

EXAMPLE 6

Pattern of Inhibition of Representative Microorganisms Using Silicone Emulsion $CO_2$ Sensors Microtiter plates (96 flat bottom wells) containing 0.5% xylenol blue silicone-emulsion sensors were filled with 100 microliters of microbial growth medium containing no inhibitors (growth control wells) and eighteen different dyes, antibiotics, and other inhibitory substances. Final concentrations of the inhibitors were achieved after addition of 100 microliters of inoculum (final inoculum of $5 \times 10^7$ CFU/ml) of the representative microorganisms. The concentrations of inhibitors were predetermined to give differences in the amount of growth (inhibition) to provide a pattern that differentiates between species of gram negative microorganisms.

After inoculating the microtiter tray, it was sealed with a pressure sensitive plastic plate sealer and initial readings were taken with a reflectance reader. The plate was then placed into a 37° C. incubator. After four hours incubation, the plate was removed and final reflectance readings were taken.

The results in Table 3 show a pattern of growth, no growth, or intermediate growth of the four test organisms with the eighteen inhibitors. The pattern of inhibition is clearly different for each of the microbial species tested, thus distinguishing that organism from other species.

TABLE 3

PATTERN OF INHIBITION OF REPRESENTATIVE MICROORGANISMS USING SILICONE-EMULSION SENSORS

| INHIBITORY AGENT | Escherichia coli 33582[1] | Proteus mirabilis 33583 | Pseudomonas aeruginosa 33584 | Alcaligenes odorans 33585 |
|---|---|---|---|---|
| Acriflavine 30 mcg[3] | 5%[2] | 68% | 84% | 55% |
| Brilliant green 3 mcg | 104% | 84% | 101% | 37% |
| Cobalt chloride 205 mcg | 27% | 17% | 52% | 35% |
| Cycloserine 78 mcg | 13% | 107% | 56% | 116% |
| Cycloserine | 8% | 26% | 66% | 27% |

TABLE 3-continued

PATTERN OF INHIBITION OF
REPRESENTATIVE MICROORGANISMS
USING SILICONE-EMULSION SENSORS

| INHIBITORY AGENT | Escherichia coli 33582[1] | Proteus mirabilis 33583 | Pseudomonas aeruginosa 33584 | Alcaligenes odorans 33585 |
|---|---|---|---|---|
| 240 mcg | | | | |
| Dibromosalicyclic acid 750 mcg | 83% | 38% | 88% | 25% |
| Dodecylamine 18.75 mcg | 99% | 108% | 118% | 106% |
| Floxuridine 36 mcg | 55% | 35% | 79% | 75% |
| Malachite green 3 mcg | 40% | 107% | 87% | 66% |
| Methylene blue 255 mcg | 20% | 80% | 90% | 56% |
| Omadine disulfide 5.5 mcg | 10% | 71% | 94% | 36% |
| Sodium azide 75 mcg | 6% | 35% | 47% | 47% |
| Thallous acetate 150 mcg | 40% | 68% | 34% | 47% |
| Carbenicillin 40 mcg | 54% | 69% | 89% | 77% |
| Cephalothin 13.5 mcg | 53% | 26% | 108% | 66% |
| Colistin 13 mcg | 3% | 114% | 34% | −44% |
| Kanamycin 5.4 mcg | 66% | 44% | 105% | 95% |
| Novobiocin 48 mcg | 9% | 48% | 85% | 16% |

[1]American Type Culture Collection (ATCC) number
[2]Percent growth in the presence of the antibiotic as compared to a growth control without antibiotics. Growth is determined by the amount of reflectance from the emulsion sensor which is a measure of the amount of carbon dioxide produced.

As described above, existing technologies for microbial testing rely on visual or photometric determination of turbidity resulting from growth of the test organism or growth determination by utilization of fluorogenic substrates. The polymer-emulsion $CO_2$ sensors of the invention determine growth by the amount of $CO_2$ being generated by the test organism.

Antimicrobial Susceptibility

Our $CO_2$ sensor technology can be used with three antimicrobial susceptibility methodologies. The first method is the classical method of determining minimal inhibitory concentrations (MIC) of antibiotics to a test organism. Serial two-fold dilutions of selected antibiotics, in concentrations spanning the systemic therapeutic range, are made in microtiter wells containing growth medium and $CO_2$ sensors. The wells are inoculated with approximately $10^5$ CFU/ml of the test organism and the wells are sealed. The plate is incubated at 37° C. for 24 hours. Following incubation, the minimum inhibitory concentration for a particular antibiotic is the well with the highest dilution that shows no change in the sensor, determined visually or by measuring reflectance, indicating no $CO_2$ production and thus no growth of the test organism.

The second method is a rapid MIC determination using two predetermined concentrations of an antibiotic that span the useful systemic therapeutic range and a growth control well. The wells are inoculated with approximately $10^6$-$10^7$ CFU/ml of the test organism, sealed, and incubated at 37° C. for 3-6 hours. During the incubation period, the $CO_2$ sensors are monitored using a reflectometer, by taking continuous, periodic or initial and final readings. The minimal inhibitory concentration of an antibiotic for a particular microorganism can be determined from regression analysis of values determined from rate, acceleration, or total $CO_2$ production.

The third method of susceptibility testing is also a rapid method that requires 3-6 hours of incubation. However, this method uses only one concentration of the antibiotic in the growth medium. A growth control is included and an inoculum of approximately $10^5$-$10^7$ CFU/ml of the test organism is required. The sensors are monitored for $CO_2$ production and comparison with pre-established criteria indicates whether the test organism is sensitive, intermediate, or resistant to a particular antibiotic.

Pure strains of microorganisms isolated using standard microbiological techniques from patient specimens can be used with this $CO_2$ sensor system. The great advantage offered by the invention is, however, that direct inoculation with patient specimens or blood cultures is feasible without having to isolate the organisms, because growth detection with this system is not affected by interfering substances, such as those found in blood or other body fluids. The patient specimens of blood or other body fluids may first be cultured by incubation in order to expand the microorganism population. The specimen may be used for direct inoculation, even after culturing.

EXAMPLE 7

Antimicrobial Susceptibility Pattern of Representative Microorganisms Using Silicone-Emulsion $CO_2$ Sensors Microtiter plates (96 flat bottom wells) containing 0.05% Xylenol blue silicone-emulsion sensors on the bottom were filled with 100 microliters of microbial growth medium containing no antibiotics) growth control wells) and nine different classes of antibiotics. Final concentrations of the antibiotics were achieved after addition of 100 microliters of inoculum (final inoculum of $5 \times 10^7$ CFU/ml) of the representative microorganisms. The concentrations of antibiotics used represents those used in determining if the test organism is sensitive, intermediate, or resistant to a particular antibiotic.

After inoculating the microtiter tray, it was sealed with a pressure sensitive plastic plate sealer and initial readings were taken with a reflectance reader. The plate was then placed into a 37° C. incubator. After four hours incubation, the plate was removed and final reflectance readings were taken.

The results in Table 4 show a pattern of growth, no growth, or intermediate growth of the four test organisms with the nine classes of antibiotics. This is indicative of the type of susceptibility of the organisms to the antibiotics. The organisms tested vary in their susceptibility pattern because of differences in their physiological makeup.

TABLE 4

ANTIMICROBIAL SUSCEPTIBILITY PATTERN
OF REPRESENTATIVE MICROORGANISMS
USING SILICONE-EMULSION $CO_2$ SENSORS

| | MICROORGANISM | | | |
|---|---|---|---|---|
| ANTIBIOTIC | Escherichia coli 29194[1] | Pseudomonas aeruginosa 27853 | Staphylococcus aureus 25923 | Streptococcus faecalis 29212 |
| Methicillin 5 mcg[3] | 111%[2] | 146% | 16% | 116% |
| Penicillin G 0.2 units | 103% | 149% | 45% | 108% |

TABLE 4-continued
ANTIMICROBIAL SUSCEPTIBILITY PATTERN OF REPRESENTATIVE MICROORGANISMS USING SILICONE-EMULSION $CO_2$ SENSORS

| ANTIBIOTIC | MICROORGANISM | | | |
|---|---|---|---|---|
| | Escherichia coli 29194[1] | Pseudomonas aeruginosa 27853 | Staphylococcus aureus 25923 | Streptococcus faecalis 29212 |
| Kanamycin 22 mcg | 91% | 72% | 13% | 95% |
| Chloramphenicol 4 mcg | 14% | 88% | 45% | 91% |
| Tetracycline 0.5 mcg | 76% | 120% | 15% | 109% |
| Vancomycin 10 mcg | 94% | 106% | 22% | 15% |
| Nalidixic acid 15 mcg | 18% | 109% | 80% | 116% |
| Nitrofurantoin 15 mcg | 14% | 112% | 33% | 110% |
| Trimethoprim/ Sulfa 18 mcg | 88% | 86% | 86% | 80% |

[1]American Type Culture Collection (ATCC) number
[2]Percent growth in the presence of the antibiotic as compared to a growth control without antibiotics. Growth is determined by the amount of reflectance from the emulsion sensor which is a measure of the amount of carbon dioxide produced.
[3]Micrograms per milliliter.

We claim:

1. A device for continuously monitoring biological activity in a specimen comprising a sealable specimen container with a sealing means, having an internal chamber in which a specimen may be cultured with a culture medium, having at least one transparent section and a sensor means located inside said container in the region of the transparent section, whereby changes in the appearance of the sensor means can be continuously monitored from the exterior of said container through said transparent section, thereby monitoring biological activity without violating the integrity of said container after sealing, said sensor means comprising a membrane and an indicator medium, the indicator medium being selected for its ability to exhibit a detectable change when exposed to products of an organism's metabolic activity.

2. The device according to claim 1, wherein the sealing means used to seal said container comprises said transparent section.

3. The device according to claim 1, wherein said sealing means incorporates said sensor means.

4. The device of claim 3, wherein the sensor means comprises a charged membrane.

5. The device of claim 4, wherein the sensor means comprises a positively charged membrane.

6. The device of claim 4, wherein the sensor means comprises a negatively charged membrane.

7. The device of claim 4, wherein the sensor means comprises a positively charged nylon membrane.

8. The device of claim 1 comprising a multiplicity of separate specimen containers, wherein at least one of the containers has a sensor located therein.

9. The device of claim 8, comprising a microtiter plate.

10. The device of claim 8, wherein said sensor is introduced into each container as a liquid emulsion, which is cured in situ.

11. The device of claim 10, wherein the emulsion is introduced into each container by spraying.

12. A device according to claim 1, wherein said sensor means is sprayed onto said transparent section.

13. The device of claim 1, wherein the indicator medium comprises at least one molecular species responsive to pH.

14. The device of claim 13, wherein the indicator medium comprises a combination of molecular species responsive to a range of pH.

15. The device of claim 1, wherein the indicator medium is a molecular species responsive to the presence of $NH_3$.

16. The device of claim 1, wherein the sensor means comprises a charged membrane.

17. The device of claim 1, wherein the membrane of the sensor means is bonded to the interior surface of said container.

18. The device of claim 17, wherein the membrane of the sensor means is at least circumferentially bonded to the interior surface of the container.

19. The device of claim 1, wherein the sensor means is separated from the specimen in said container by a semipermeable membrane.

20. The device of claim 19, wherein the semipermeable membrane comprises a membrane formed in situ.

21. The device of claim 1, wherein the sensor means comprises droplets of indicator medium immobilized within a polymer matrix and the polymer matrix makes up the membrane.

* * * * *